US011213505B2

(12) United States Patent
Baldacci

(10) Patent No.: US 11,213,505 B2
(45) Date of Patent: Jan. 4, 2022

(54) PRODUCT BASED ON IRON BIS-GLYCINATE CHELATE AND ALGINIC ACID AND/OR WATER-SOLUBLE SALTS THEREOF, FORMULATIONS THEREOF, AND PHARMACEUTICAL USES THEREOF

(71) Applicant: LABORATORI BALDACCI S.P.A., Pisa (IT)

(72) Inventor: Massimo Baldacci, Pisa (IT)

(73) Assignee: LABORATORI BALDACCI S.P.A., Pisa (IT)

(*) Notice: Subject to any disclaimer, the term of this patent is extended or adjusted under 35 U.S.C. 154(b) by 0 days.

(21) Appl. No.: 16/816,878

(22) Filed: Mar. 12, 2020

(65) Prior Publication Data
US 2020/0206181 A1 Jul. 2, 2020

Related U.S. Application Data

(63) Continuation-in-part of application No. 15/575,278, filed as application No. PCT/IB2016/054199 on Jul. 14, 2016, now abandoned.

(30) Foreign Application Priority Data

Jul. 17, 2015 (IT) .......................... 102015000035481

(51) Int. Cl.
*A61K 31/295* (2006.01)
*A61P 7/06* (2006.01)
*A61K 9/16* (2006.01)

(52) U.S. Cl.
CPC .......... *A61K 31/295* (2013.01); *A61K 9/1652* (2013.01); *A61P 7/06* (2018.01)

(58) Field of Classification Search
USPC ....................................................... 514/502
See application file for complete search history.

(56) References Cited

U.S. PATENT DOCUMENTS 6,455,052 B1 * 9/2002 Marcussen ............. A61K 9/286
424/234.1
2003/0190355 A1  10/2003 Hermelin et al.

FOREIGN PATENT DOCUMENTS

| CN | 1280260 C | * | 10/2006 |
|----|-----------|---|---------|
| CN | 100344326 C | | 10/2007 |
| CN | 101322778 A | | 12/2008 |
| EP | 2799074 | * | 11/2010 |
| WO | 2009083561 A1 | | 7/2009 |

OTHER PUBLICATIONS

XP-002754924, Nov. 2006, Huang.*
Ashmead (Archives Latinoamericanos de Nutricion, Suplemento vol. 51, No. 1, 2001, pp. 13-21).*
International Search Report dated Oct. 18, 2016 in International Application No. PCT/IB2016/054199.
"Opinion of the Scientific Panel on Food Additives, Flavourings, Processing Aids and materials in Contact with Food on a request from the Commission related to Ferrous bisglycinate as a source of iron for use in the manufacturing of foods and in food supple", The EFSA Journal (2006) 299, Jan. 6, 2006, pp. 1-17.
Ashmead, "The chemistry of ferrous bis-glycinate chelate.", Arch. Latino Am. de Nutr., vol. 51 No. 1, 2001, pp. 7-12.
Ashmead, "The absorbtion and metabolism of iron amino acid chelate", Arch. Latino Am. de Nutr., vol. 51 No. 1, 2001, pp. 13-21.
"Chapter 11, Microcapsules, Inclusion compounds and Solid Dispersions", Pamphlet Series for National Qualification Examination of Licensed Pharmacists, China Medical Science and Technology Press, (Jan. 2012) (with English Translation).
"Complete Handbook of Chinese OTC Drugs", p. 76, Shaanxi Science and Technology Press (2005) (with English Translation).
Coplin, et al., "Tolerability of Iron: a comparison of bis-glycino iron II and ferrous sulphate", Clinical Therapeutics, vol. 13, n.5, 1991, pp. 606-612.
Jeppsen, "Toxicology and safety of Ferrochel and other iron amino acids chelates", Arch. Latino Am. de Nutr., vol. 51 No. 1, 2001, pp. 26-34.
Marchetti, et al., "Comparison of the Rates of Vitamin Degradation when Mixed with Metal Sulphates or Metal Amino Acid Chelates", Journal of Food Composition and Analysis (2000) vol. 13, Issue 6, Dec. 2000, pp. 875-884.
"Chapter 2, Fundamentals of Clinical Nutrition", Nutrition and Diet Guidelines, People's Military Medical Press, (Mar. 2015) (with English Translation).
Pineda, et al., "Effectiveness of iron amino acids chelate on the treatment of iron deficiency anaemia in adolescents", Journal of appl. Nutr., vol. 46, Nos. 1-2, 1994, 13 pages.
Pineda, et al., "Effectiveness of Treatment of Iron-Deficiency Anemia in Infants and Young Children With Ferrous Bis-glycinate Chelate", Nutrition, 17(5), 2001, pp. 381-384.
Abstract, Application 20010061.1, Aug. 8, 2003, (with English Translation).
Horniblow, R. D. et al., "Alginate-Iron Speciation and Its Effect on In Vitro Cellular Iron Metabolism," PLOS ONE, Sep. 2015, doi:10.1371/journal.pone.0138240, 14 pages.
Wawer, A. A. et al., "Alginate Inhibits Iron Absorption from Ferrous Gluconate in a Randomized Controlled Trial and Reduces Iron Uptake into Caco-2 Cells," PLOS ONE, Nov. 2014, vol. 9(11), 8 pages.
Wolbling, R. H. et al., "Inhibition of the Intestinal Absorption of Iron by Sodium Alginate and Guar Gum in Rats," Digestion 20:403-409 (1980).

* cited by examiner

*Primary Examiner* — Kathrien A Cruz
(74) *Attorney, Agent, or Firm* — Rothwell, Figg, Ernst & Manbeck, P.C.

(57) ABSTRACT

The object of the present invention is a product obtainable by spray-drying an aqueous solution comprising iron bis-glycinate chelate and alginic acid and/or water-soluble salts thereof, preferably sodium alginate, potassium alginate and/or magnesium alginate, the use of said product for the prevention and/or treatment of anaemia, preferably sideropenic anaemia, in humans, the pharmaceutical formulations containing it, and the use of said formulations for the prevention and/or treatment of anaemia, preferably sideropenic anaemia, in humans.

11 Claims, 4 Drawing Sheets

PRODUCT BASED ON IRON BIS-GLYCINATE CHELATE AND ALGINIC ACID AND/OR WATER-SOLUBLE SALTS THEREOF, FORMULATIONS THEREOF, AND PHARMACEUTICAL USES THEREOF

This application is a continuation-in-part of U.S. application Ser. No. 15/575,278, filed Nov. 17, 2017; which is a National Stage of International Application PCT/IB2016/054199, filed Jul. 14, 2016, published Jan. 26, 2017, under PCT Article 21(2) in English; which claims the priority of Italian Application No. 102015000035481, filed Jul. 17, 2015. The contents of the above-identified applications are incorporated herein by reference in their entireties.

DESCRIPTION

The object of the present invention is a product obtainable by spray-drying an aqueous solution comprising iron bis-glycinate chelate and alginic acid and/or water-soluble salts thereof, preferably sodium alginate, potassium alginate and/or magnesium alginate, the use of said product for the prevention and/or treatment of anaemia, preferably sideropenic anaemia, in humans, the pharmaceutical formulations containing it, and the use of said formulations for the prevention and/or treatment of anaemia, preferably sideropenic anaemia, in humans.

The oral administration of iron salts has long been recognised as the treatment of choice to treat anaemia in humans.

Inorganic salts of divalent iron are generally used, which in most cases exhibit poor bioavailability and side effects in a high percentage of patients.

In the literature it has been reported how the iron bis-glycinate chelate product (Ferrochel®) significantly differs from the other ferrous salts, both as regards to the increased absorption through the gastro-intestinal mucosa and the improved safety profile, as indicated below.

Iron bis-glycinate chelate has the following structural formula (I):

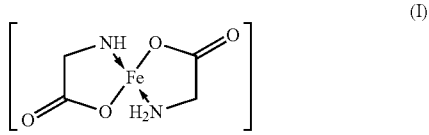

This compound, and the structure thereof, are long well known (Ashmed S. D. The chemistry of ferrous bis-glycinate chelate, *Arch. Latino Am. De Nutr.*, 2001, 51(1), 7-12; Coplin et al. Tolerability of Iron: a comparison of bis-glycino iron II and ferrous sulphate, *Clinical Therapeutics*, vol. 13, n.5, 606-612, 1991).

Iron bis-glycinate chelate is a rather soluble chelate complex characterised by a metal centre, Fe(II), tetracoordinated by two identical chelants (glycine). The dative bond of the nitrogen atom contributes to stabilising the energy of the metal centre orbitals and the ligand geometry through the formation of a five-atom ring.

This compound is also known for its tolerability, safety and high bioavailability (Jeppsen R. B. Toxicology and safety of Ferrochel and other iron amino acids chelates, *Arch. Latino Am. de Nutr.*, 2001, 51(1), 26-34; Opinion of the scientific Panel on Food additives, Flawouring Processing Aids and materials in contact with Food on a request from the Commision related to: Ferrous bisglycinate as a source of iron for use in the manufacturing of foods and in foods supplements, *EFSA Journal*, 2006, 299, 1-17).

The literature data show that such a chelate complex has a higher bioavailability with respect to iron mineral salts, such as ferrous sulphate, since it is absorbed as it is at the intestinal mucosa level and thus it does not undergo any chemical modification in the gastrointestinal apparatus (Pineda O. et al., Effectiveness of iron amino acids chelate on the treatment of iron deficiency anaemia in adolescents, *Journal of appl. Nutr.*, Vol. 46, Numbers 1-2, 1994; Pineda O., Effectiveness of treatment of iron deficiency anaemia in infants and young children with ferrous bis-glycinate chelate, *Nutrition*, 17(5), 2001, 381-84).

The stability of the bond, proven by the fact that the product does not undergo hydrolysis at different pH values of the gastrointestinal tract, and the low molecular weight (204 g/mol) allow maximum absorption when administered orally (DeWayne H. A., The absorbtion and metabolism of iron amino acid chelate, *Arch. Latino Am. de Nutr.*, 2001, 51(1), 13-21; Marchetti M et al., Comparison of the rates of vitaminic degradation when mixed with metal sulphates or metal amino acids chelates, *J. Food Comp. Anal.*, 2000, 13, 875-884).

Moreover, the oral absorption of iron bis-glycinate chelate does not show any interference with food or other active principles.

However, iron bis-glycinate chelate, like other products containing iron, is found to have a very unpleasant taste, characteristic of the iron complex contained therein and, more generally, of all the products containing iron which, notoriously, are therefore not easy to administrate due to their low palatability.

In addition, side effects such as heartburn have been highlighted for it as well, albeit in much smaller percentage and with less severity than other iron salts. In particular, for iron bis-glycinate chelate these side effects are shown when the same is used in high doses. The need is therefore felt for a product based on iron bis-glycinate chelate for the prevention and/or treatment of anaemia, preferably sideropenic anaemia, in humans, that it is readily absorbed, safe, with an improved palatability, administrable by oral route, and free of side effects after such administration.

The term "anaemia" according to the present invention comprises sideropenic anaemia, aplastic anaemia, vitamin and/or folate deficiency anaemia (such as, for example, pernicious anaemia), chronic disease anaemia (such, as for example, AIDS, cancer or hepatitis) and haemolytic anaemia; it preferably refers to sideropenic anaemia. Sideropenic anaemia is a form of anaemia characterised by a significant decrease of haemoglobin in the circulating blood which is caused by iron deficiency.

It has been, therefore, surprisingly found a stable product based on iron bis-glycinate chelate and alginic acid and/or water-soluble salts thereof, preferably sodium alginate, potassium alginate and/or magnesium alginate, which addresses the needs indicated above.

Alginic acid is a copolymer composed of a series of polysaccharide polyanions formed by repeated units of β-D-mannuronic and α-L-glucuronic acid linked together by 1→4 bonds. The product is isolated from various species of algae and has an average molecular weight which can vary from a few thousands Dalton (Da) up to 350,000 Da.

The physical and chemical properties of alginic acid depend on the ratio between glucuronic acid and D-mannuronic acid.

The product is recognised by the FDA as a safe product from a toxicological point of view, i.e. it is defined as GRAS (Generally Referred as Safe), and it is used in therapy as the sodium salt in disorders related to acid secretion, gastroesophageal reflux, heartburns and acid regurgitation.

Alginates are salts of the alginic acid. The alginates of alkali metals, in particular sodium alginate, potassium alginate, and magnesium alginate are soluble in water, while calcium alginate is not water-soluble.

The product based on iron bis-glycinate chelate and alginic acid and/or water-soluble salts thereof object of the present invention is characterised by being obtained by a spray-drying process of an aqueous solution comprising iron bis-glycinate chelate and alginic acid and/or the water-soluble salts thereof.

The product thus obtained, completely safe from the toxicological point of view (safety), is characterised by a high surface area which allows its rapid absorption, with protective properties at the level of the gastrointestinal mucosa itself. In addition, this product has an improved palatability compared to iron bis-glycinate chelate alone, which allows its use in buccal and chewable formulations, and in oral solutions, achieving an improved adherence to the medical scheme (compliance) by the patient.

The alginic acid and/or the water-soluble salts thereof, preferably sodium alginate, potassium alginate, and/or magnesium alginate, particularly preferred for the spray-drying with iron bis-glycinate chelate has a low viscosity, with a molecular weight preferably comprised between 10,000 and 15,000 Da (for example, Protanal® LFR), but also alginic acid and/or water-soluble salts thereof with a molecular weight preferably comprised between 40,000 and 50,000 Da (for example, Protanal® LFR 5/60), comprised between 90,000 and 200,000 Da (for example, Protanal® CR 8133) or comprised between 250,000 and 350,000 Da (for example, Protanal® CR 8233) may be used.

Therefore, the molecular weight of the alginic acid and/or water-soluble salts thereof, preferably sodium alginate, potassium alginate and/or magnesium alginate, usable for spray-drying the iron bis-glycinate chelate to obtain the product of the present invention is comprised between 10,000 and 350,000 Da, preferably between 10,000 and 250,000 Da, being the range between 10,000 and 15,000 Da the most preferred.

The preferred weight ratio between the iron bis-glycinate chelate and the alginic acid and/or the water-soluble salts thereof, preferably sodium alginate, potassium alginate and/or magnesium alginate, in the product obtained by spray-drying are comprised in the range of 1-2:1-3, and they are preferably 1:1, 1:2 or 2:3.

The peculiarity of the spray-drying process of an aqueous solution comprising the iron bis-glycinate chelate and the alginic acid and/or water-soluble salts thereof, preferably sodium alginate, potassium alginate and/or magnesium alginate is the obtainment of a dry powder in which the weight proportion present in the aqueous starting solution are maintained.

Therefore, the preferred weight ratios between the iron bis-glycinate chelate and the alginic acid and/or water-soluble salts thereof, preferably sodium alginate, potassium alginate and/or magnesium alginate, in the aqueous solution used for spray drying are comprised in the range of 1-2:1-3, and preferably they are 1:1, 1:2, or 2:3.

In particular, it is preferred a product obtained by spray-drying an aqueous solution containing iron bis-glycinate chelate and alginic acid and/or water-soluble salts thereof, preferably sodium alginate, potassium alginate and/or magnesium alginate with a molecular weight comprised between 10,000 and 15,000 Da, wherein the weight ratio between the iron bis-glycinate chelate and the alginic acid and/or water-soluble salts thereof, preferably sodium alginate, potassium alginate and/or magnesium alginate, is comprised in the range of 1-2:1-3, and preferably it is 1:1, 1:2 or 2:3.

Most preferred is a product obtained by spray-drying an aqueous solution containing iron bis-glycinate chelate and sodium alginate (Protanal® LFR), with a molecular weight comprised between 10,000 and 15,000 Da, wherein the weight ratio between the iron bis-glycinate chelate and the sodium alginate, is comprised in the range of 1-2:1-3, preferably it is 1:1, 1:2 or 2:3, and even more preferably it is 1:1.

According to another preferred aspect, the aqueous solution used for spray-drying is obtained by solution of iron bis-glycinate chelate and alginic acid and/or water-soluble salts thereof, preferably sodium alginate, potassium alginate and/or magnesium alginate, which preferably has a molecular weight comprised between 10,000 and 15,000 Da, in a weight ratio with water of 1:10 and 1:12, respectively.

According to a further preferred aspect, the particle size of the product in powder form obtained after spray-drying the aqueous solution comprising the iron bis-glycinate chelate and the alginic acid and/or water-soluble salts thereof, preferably sodium alginate, potassium alginate and/or magnesium alginate, is less than 20μ.

According to a further preferred aspect, the aqueous solution comprising the iron bis-glycinate chelate and the alginic acid and/or water-soluble salts thereof, preferably sodium alginate, potassium alginate and/or magnesium alginate, may comprise an antioxidant, preferably in an amount lower than 0.5% of the total weight of the iron bis-glycinate chelate and the alginic acid and/or water-soluble salts thereof, and even more preferably in an amount lower than 0.3%, where said percentages are referred to the total weight of the iron bis-glycinate chelate and the alginic acid and/or water-soluble salts thereof. Preferably said antioxidant is ascorbic acid.

According to a further aspect of the invention, the residual moisture value in the product in dry powder form obtained after spray-drying the aqueous solution comprising the iron bis-glycinate chelate and the alginic acid and/or water-soluble salts thereof, preferably sodium alginate, potassium alginate and/or magnesium alginate, is comprised between 2.60% and 2.90%.

In addition, according to a further aspect of the invention, the density of the product in dry powder form obtained after spray-drying the aqueous solution comprising the iron bis-glycinate chelate and the alginic acid and/or water-soluble salts thereof, preferably sodium alginate, potassium alginate and/or magnesium alginate, was found to be comprised between 0.2 g/ml and 0.8 g/ml, preferably between 0.3 g/ml and 0.6 g/ml, and even more preferably between 0.4 g/ml and 0.5 g/ml.

An object of the present invention is, therefore, a product obtainable by spray-drying an aqueous solution comprising iron bis-glycinate chelate and alginic acid and/or water-soluble salts thereof, preferably sodium alginate, potassium alginate and/or magnesium alginate, as indicated above, for use in the prevention and/or treatment of anaemia, preferably sideropenic anaemia, in humans.

The product obtainable by spray-drying an aqueous solution comprising iron bis-glycinate chelate and alginic acid and/or water-soluble salts thereof, preferably sodium alginate, potassium alginate and/or magnesium alginate, as indicated above is administered orally, preferably formulated in a solid, semi-solid or liquid form, said solid form being selected from tablet, granulate, microgranulate or capsule, and said semi-solid or liquid form selected from suspension (aqueous or oily) or solution.

Objects of the present invention are, therefore, the oral pharmaceutical forms comprising the product obtainable by spray-drying an aqueous solution comprising the iron bis-glycinate chelate and the alginic acid and/or water-soluble salts thereof, preferably sodium alginate, potassium alginate and/or magnesium alginate, as indicated above, optionally together with physiologically acceptable excipients.

According to the invention, the term "physiologically acceptable excipient" means a substance devoid of any pharmacological effect of its own, and that does not produce adverse reactions when administered to a mammal, preferably a human being. Pharmaceutically acceptable excipients are well known in the art and are described, for example, in *Handbook of Pharmaceutical Excipients*, sixth edition 2009, incorporated herein by reference.

According to the invention, the tablet, granulate and microgranulate may be in coated, non-coated and/or effervescent and/or buccal and/or chewable form, preferably in the form of an effervescent tablet, buccal tablet, or chewable tablet.

The term "effervescent" according to the present invention means a form that is able to develop carbon dioxide when in contact with water and/or with the buccal environment, in the presence of saliva.

In order to obtain the effervescent form of the invention, bi-carboxylic acids, tri-carboxylic acids, or a mixture thereof are preferably used.

More preferably, the effervescent compositions according to the invention are formulated with sodium citrate dihydrate and monohydrate, sodium carbonate, sodium bicarbonate, potassium bicarbonate, citric acid, tartaric acid, adipic acid, monosodium phosphate, alginic acid, magnesium hydroxycarbonate, or a mixture thereof.

According to a preferred embodiment, the capsules comprising the product obtainable by spray-drying an aqueous solution comprising iron bis-glycinate chelate and alginic acid and/or water-soluble salts thereof, preferably sodium alginate, potassium alginate and/or magnesium alginate, as indicated above, may be coated.

In particular, in the solid oral forms of the invention the product obtainable by spray-drying an aqueous solution comprising iron bis-glycinate chelate and alginic acid and/or water-soluble salts thereof, preferably sodium alginate, potassium alginate and/or magnesium alginate according to the invention in a ratio of 1:1, is contained in an amount ranging from about 10 mg to about 400 mg of iron bis-glycinate chelate and alginic acid polymer (tolerance of about 0.5% by weight) (corresponding to from about 1 mg to about 40 mg of iron ion), preferably from about 20 mg to about 350 mg (i.e. corresponding to from about 2 mg to about 35 mg of iron ion), more preferably from about 100 mg to about 300 mg (corresponding to from about 10 mg to about 30 mg of iron ion).

Conversely, in the solid oral forms of the invention the product obtainable by spray-drying an aqueous solution comprising iron bis-glycinate chelate and alginic acid and/or water-soluble salts thereof, preferably sodium alginate, potassium alginate and/or magnesium alginate according to the invention in a ratio of 1:2, is contained in an amount ranging from about 20 mg to about 800 mg of iron bis-glycinate chelate and alginic acid polymer (tolerance of about 0.5% by weight) (corresponding to from about 1 mg to about 40 mg of iron ion), preferably from about 40 mg to about 750 mg (i.e. corresponding to from about 2 mg to about 35 mg of iron ion), more preferably from about 200 mg to about 600 mg (corresponding to from about 10 mg to about 30 mg of iron ion).

According to a further preferred aspect, in the solid oral forms of the invention the product obtainable by spray-drying an aqueous solution comprising iron bis-glycinate chelate and alginic acid and/or water-soluble salts thereof, preferably sodium alginate, potassium alginate and/or magnesium alginate according to the invention in a ratio of 2:3, is contained in an amount ranging from about 15 mg to about 600 mg of iron bis-glycinate chelate and alginic acid polymer di (tolerance of about 0.5% by weight) (corresponding to from about 1 mg to about 40 mg of iron ion), preferably from about 30 mg to about 525 mg (i.e. corresponding to from about 2 mg to about 35 mg of iron ion), more preferably from about 150 mg to about 450 mg (corresponding to from about 10 mg to about 30 mg of iron ion).

In a preferred embodiment of the present invention, said solid oral form is a tablet, more preferably an effervescent tablet, or a buccal or chewable tablet.

In a further preferred embodiment of the present invention, said solid oral form is a capsule.

Preferred capsules of the invention may comprise bulking agents, such as for example dicalcium phosphate, coating agents, such as for example hydroxypropyl methylcellulose, anti-caking agents, such as for example silicon dioxide, agglomerating agents, such as for example magnesium salts of fatty acids, and colourants, such as for example titanium dioxide.

In the semi-solid or liquid pharmaceutical forms, the product obtainable by spray-drying an aqueous solution comprising iron bis-glycinate chelate and alginic acid and/or water-soluble salts thereof, preferably sodium alginate, potassium alginate and/or magnesium alginate according to the invention is contained in a quantity ranging from 1 to 10 g/100 ml of solution/suspension (corresponding to from 2 to 20 mg of iron ion/ml).

The product obtainable by spray-drying an aqueous solution comprising iron bis-glycinate chelate and alginic acid and/or water-soluble salts thereof, preferably sodium alginate, potassium alginate and/or magnesium alginate, according to the invention may also be formulated in association with at least one sweetener and/or flavour.

Said at least one sweetener and/or flavour according to the invention may preferably be selected from acesulfame K, sucralose, sorbitol, sucrose, fructose, orange flavour, lemon flavour, mandarin flavour, caramel flavour, or a mixture thereof.

More particularly, the product obtainable by spray-drying an aqueous solution comprising iron bis-glycinate chelate and alginic acid and/or water-soluble salts thereof, preferably sodium alginate, potassium alginate and/or magnesium alginate, according to the invention is preferably formulated in association with a mixture comprising acesulfame K, sucralose, sorbitol and flavour, where the weight ratio between acesulfame K:sucralose:sorbitol:flavour is of about 1:0.30-0.50:0.12-0.24:3.00-3.40 by weight, respectively. According to the present invention, said weight ratio is preferably of about 1:0.40:0.18:3.20 by weight.

The product obtainable by spray-drying an aqueous solution comprising iron bis-glycinate chelate and alginic acid and/or water-soluble salts thereof, preferably sodium alginate, potassium alginate and/or magnesium alginate, according to the invention may also be formulated in association with additional physiologically acceptable excipients and/or additives, such as for example acidifiers and/or preservatives (ascorbic acid, parabens).

According to a further embodiment, the product obtainable by spray-drying an aqueous solution comprising iron bis-glycinate chelate and alginic acid and/or water-soluble salts thereof, preferably sodium alginate, potassium alginate and/or magnesium alginate of the invention may be administered in association with one or more additional active principles.

Additional active principles according to the present invention may preferably be selected from vitamins and/or mineral salts.

Said vitamins may preferably be selected from vitamin B9 (folic acid), vitamin B12 and/or vitamin B6.

Said mineral salts may preferably be selected from potassium, magnesium, iodine, zinc salts.

The product obtainable by spray-drying an aqueous solution comprising iron bis-glycinate chelate and alginic acid and/or water-soluble salts thereof, preferably sodium alginate, potassium alginate and/or magnesium alginate, according to the present invention may be administered as the sole therapy, or following a conventional therapy, both oral and parenteral (for example, iron sulphate).

Objects of the present invention are also the oral pharmaceutical forms comprising the product obtainable by spray-drying an aqueous solution comprising iron bis-glycinate chelate and alginic acid and/or water-soluble salts thereof, preferably sodium alginate, potassium alginate and/or magnesium alginate as indicated above, for use in the prevention and/or treatment of anaemia, preferably sideropenic anaemia, in humans.

EXAMPLES

Example 1

Iron bis-glycinate chelate and sodium alginate with a molecular weight comprised between 10,000 and 15,000 Da (Protanal® LFR Med Dev) were dissolved in water, in a weight ratio with water of 1:10 and 1:12, respectively.

The weight ratio between the iron bis-glycinate chelate and the alginic acid was 1:1.

To the solution acid ascorbic was also added, in a percentage of 0.214% with respect to the total weight of the iron bis-glycinate chelate and the sodium alginate.

The solution was placed in a mixer until dissolution was complete, then it was spray-dried by means of a spray-drying apparatus from Büchi company, using the following parameters:

Air inlet temperature: 170-190° C.
Air outlet temperature: 70-90° C.
Turbine rotation speed: 18,000-21,000 rpm
Air flow: 1,200 m$^3$/h The analysis carried out on the dried powder confirmed the total recovery of the iron in the product (97.21%) with a residual moisture value of 2.80%, while the density of the powder was found to be 0.5 g/ml and the particle size thereof was found to be less than 20μ.

Figure 1:
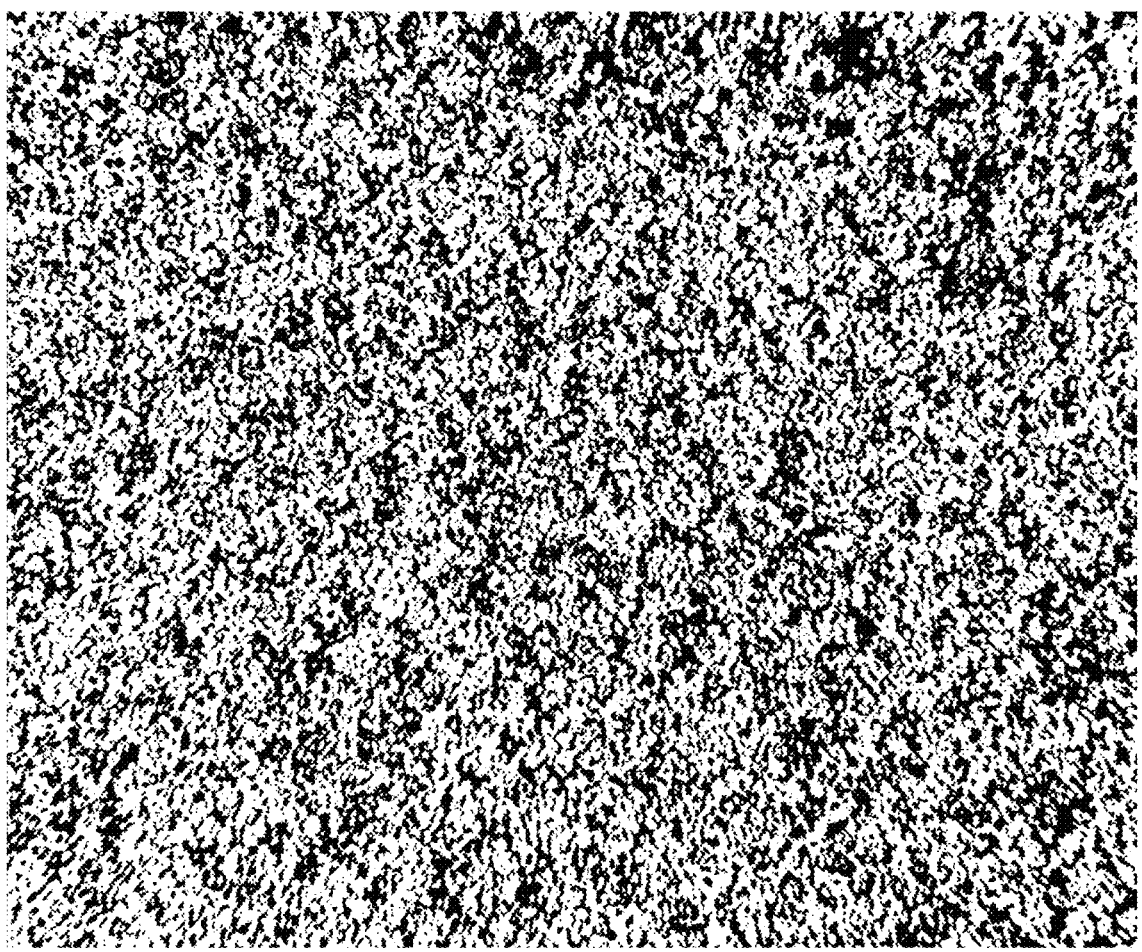
FIG. 1: Photograph of the powder obtained in Example 1, showing the product obtained by spray-drying iron bis-glycinate chelate and alginic acid (Protanal® LFR) in a ratio of 1:1. The photograph was taken with a stereomicroscope Wild Heerbrugg Makroskop M420 connected to an OPTIKAM MICROSCOPY DIGITAL USB CAMERA.
Figure 2:
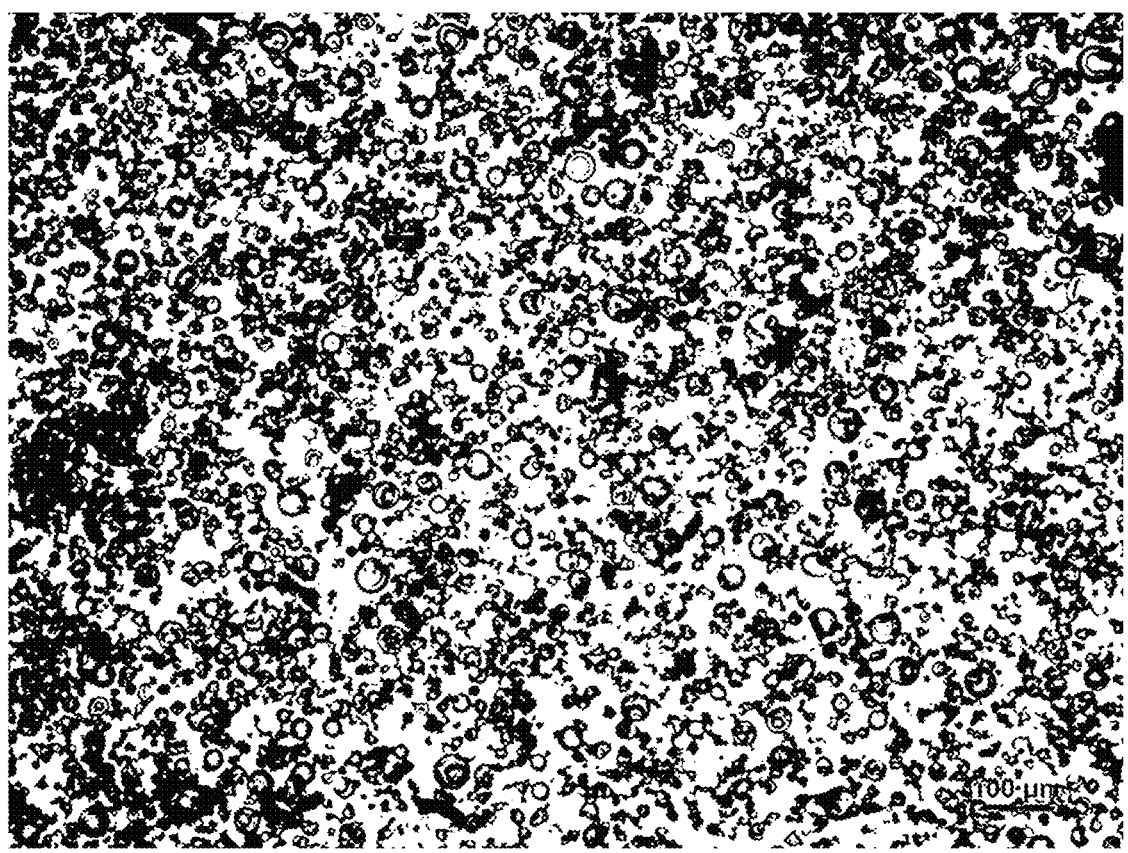
FIG. 2: Photograph of the powder obtained in Example 1, showing the product obtained by spray-drying iron bis-glycinate chelate and alginic acid (Protanal® LFR) in a ratio of 1:1. The photograph was taken with an optical microscope LEITZ DIAPLAN with a NIKON DIGITAL SIGHT DS-U1 camera.

In FIGS. 1 and 2 images of the powder obtained by the method described above are shown, obtained, respectively, with a stereomicroscope and an optical microscope, connected to a digital camera, from which it is possible to infer the formation of a product by spray-drying of iron bis-glycinate chelate and alginic acid.

Example 2

A product based on iron bis-glycinate chelate sodium alginate with the same starting materials and the same equipment of Example 1 was obtained, wherein the only differences consisted in the weight ratio between the iron bis-glycinate chelate and the alginic acid, which in the present Example is 1:2, and in the amount of ascorbic acid, which was added herein in a percentage of 0.285% with respect to the total weight of the iron bis-glycinate chelate and the sodium alginate.

The analysis carried out on the dry powder confirmed the total recovery of the iron in the product (100.04%) with a residual moisture value of 2.87%, while the density of the powder was found to be 0.5 g/m, and the particle size thereof was found to be less than 20μ.

Example 3

A product based on iron bis-glycinate chelate sodium alginate with the same starting materials and the same equipment of Example 1 was obtained, wherein the only differences consisted in the weight ratio between the iron bis-glycinate chelate and the alginic acid, which in the present Example is 2:3, and the amount of ascorbic acid, which was added herein in a percentage of 0.256% with respect to the total weight of the iron bis-glycinate chelate and the sodium alginate.

The analysis carried out on the dry powder confirmed the total recovery of the iron in the product (97.00%) with a residual moisture value of 2.63%, while the density of the powder was found to be 0.4 g/ml, and the particle size thereof was found to be less than 20μ.

Example 4

Absorption Kinetic Study

The iron bis-glycinate chelate sodium alginate obtained according to Example 1 (1:1 ratio) was formulated in capsules for oral administration with the following formulation:

TABLE 1

Capsule ingredients for a daily dose of 30 mg of iron per capsule (cps), containing iron bis-glycinate chelate sodium alginate (1:1 ratio)

| Ingredients | Mg/cps | % |
| --- | --- | --- |
| Iron bis-glycinate chelate sodium alginate (1:1 ratio) (Feralgina®) | 300.903 | 50.572 |
| Calcium phosphate (E 341ii) | 189.062 | 31.775 |
| Magnesium salts of fatty acids (E 470b) | 5.000 | 0.840 |
| Silicon dioxide (nano) (E 551) | 5.035 | 0.846 |
| Hydroxypropyl methylcellulose (E 464) | 93.176 | 15.660 |
| Titanium dioxide (E 171) | 1.824 | 0.307 |
| Total | 595 | 100 |

A capsule formulation for comparison was also prepared, whose formulation is shown in Table 2 below, containing the same excipients of the formulation according to the invention, but containing iron bis-glycinate chelate instead of iron bis-glycinate chelate sodium alginate.

TABLE 2

Capsule ingredients for a daily dose of 30 mg of iron per capsule (cps), containing iron bis-glycinate chelate

| Ingredients | Mg/cps | % |
| --- | --- | --- |
| Iron bis-glycinate chelate | 150.000 | 46.88 |
| Dibasic calcium phosphate (E 341) | 91.848 | 28.70 |
| Magnesium stearate (E 470b) | 2.152 | 0.67 |
| Silicon dioxide (E 551) | 1.000 | 0.31 |
| Hydroxypropyl methylcellulose (E 464) | 73.561 | 22.99 |
| Titanium dioxide (E 171) | 1.439 | 0.45 |
| Total | 320.000 | 100.00 |

The daily dose obtained by administration of capsules containing iron bis-glycinate chelate sodium alginate according to Table 1 and capsules containing iron bis-glycinate chelate according to Table 2 is the same, i.e. 30 mg of iron in total (Fe-ion namely Fe++, determined by an atomic absorption spectrophotometer).

Two groups of healthy adult subjects with sideropenic anaemia, of both sexes, aged between 30 and 60 years, were recruited, wherein each group consisted of five subjects. The subjects of Group I were orally administered, in the morning after an overnight fast, a capsule containing iron bis-glycinate chelate sodium alginate (Feralgina®), while the subjects of Group II were orally administered, again in the morning after an overnight fast, a capsule containing iron bis-glycinate chelate.

The two groups were fully superimposable for haemoglobin values.

Two hours following the oral administration, each subject of each group was sampled in order to assess the serum levels of iron-ion.

TABLE 3

Serum levels of Fe-ion (μg/dl) two hours after oral administration

| Patients | Product | Dose | Sideraemia T = 0 | Sideraemia T = 2 h |
| --- | --- | --- | --- | --- |
| Group I | | | | |
| 1 | Iron bis-glycinate | 30 mg | 3 | 168 |
| 2 | chelate sodium | Fe | 40 | 106 |
| 3 | alginate | | 24 | 120 |
| 4 | (Feralgina®) | | 6 | 98 |
| 5 | | | 18 | 105 |
| | | | Average = 18.2 | Average = 119 |
| Group II | | | | |
| 1 | Iron bis-glycinate | 30 mg | 25 | 104 |
| 2 | chelate | Fe | 38 | 49 |
| 3 | | | 10 | 83 |
| 4 | | | 9 | 78 |
| 5 | | | 30 | 76 |
| | | | Average = 22.4 | Average = 78 |

As it can be seen from Table 3, the serum levels of iron-ion two hours following administration of Feralgina® are significantly higher than those obtained after administration of the capsules containing iron bis-glycinate chelate, thus demonstrating the higher absorption of iron-ion at the level of the gastrointestinal mucosa which is obtained by administration of iron bis-glycinate chelate sodium alginate.

Example 5

1. Scope of the Study

The objective of the present study was to evaluate the in vitro dissolution profile of the iron bis-glycinate chelate sodium alginate (1:1 weight ratio) of example 1 (Feralgina®), in order to evidence the possible correlation between its in vitro solubility and the higher iron bioavailability compared to the administration of iron bis-glycinate chelate, as shown in example 4.

The dissolution test was performed with rotating basket apparatus according to Eur. Pharmacopoeia 9th Edition choosing hydrochloric acid to simulate the gastric fluid.

After developing a colorimetric analytical method for the determination of iron using metallic iron as standard, a series of dissolution tests were performed on the commercial product TecnoFERPlus, which contains Feralgina®; the commercial product Ferrograd (which contains iron sulphate) was chosen as reference.

A first series of assays were performed placing the product into a dialysis membrane with adequate volumes of hydrochloric acid (1.0 or 2.0 ml). In this case, the dissolution medium was 0.01 N (pH=2) hydrochloric acid, as the dialysis membrane is not compatible with pH values lower than 2.

Furthermore, the dissolution tests of TecnoFERPlus and Ferrograd were carried out by introducing a single capsule into basket of the dissolution apparatus without the presence of the dialysis membrane with hydrochloric acid solution 0.1N (pH=1.2) as dissolution medium.

2. Development of the Analytical Method

The selected analytical method involved a chemical reaction to synthesize a colorimetric complex in which the metallic iron, in hydrochloric acid solution, reacted with nitric acid oxidizing to $Fe^{3+}$. The ferric ion reacted with the potassium thiocyanate (KSCN) complexing itself according to the reaction: $Fe^{3+}+[SCN]^{-} \rightarrow [Fe(SCN)]^{2+}$ The final product was a deep red chromophore that exhibits maximum absorbance at 480 nm.

For the preparation of the stock solution, an exactly weighed amount of about 0.1 g iron powder was solubilized with concentrated HCl (36% w/v) in a 1000 ml volumetric flask. Then, known volumes of iron stock solution were diluted with volumes between 10 to 600 μl of hydrochloric acid adding then 200 μl of concentrated $HNO_3$ and 1.0 ml of 15% w/v aqueous solution of KSCN.

The reaction was carried out in a 10 ml calibrated flask and the procedure ended with the addition of water up to the fixed volume. The diluted solutions had iron concentrations ranging from 0.1 to 6.0 μg/ml.

The colorimetric method allowed to obtain absorbance values well correlated with the concentration of the solutions ($r2=0.9990$), according to a linear calibration curve described by the equation: $y=0.1493x+0.0044$.

Moreover, during the tuning of the analytical method, it was assessed whether the use of iron bis-glycinate instead of iron sulphate, could determine interference on the colorimetric analysis. The experimental method involved the preparation of samples with a known concentration of bis-glycinate iron and the addition of the previously reported reagents (nitric acid and potassium thiocyanate) to obtain a colored complex with maximum absorbance at 480 nm The concentration values calculated by using the above-reported calibration curve were consistent with the quantity of weighted bis-glycinate iron, thus confirming the applicability of the analytical method to the analysis of bis-glycinate iron.

3. Determination of the Iron Salts Dissolution Rate: Bis-Glycinate Iron (Fe Bis-Gly, Ferrochel® TRAACS, Albion) and Iron Sulphate Experimental method: the dialysis membrane (Spectrum Labs Spectra/Por 3; MWCO; 3500 kDa) was hydrated for one night (16 hours) in deionized water before the test. Then, three exactly weighted samples of bis-glycinate iron and iron sulphate having different weights (range 13-20 mg) were solubilized with 1.0 ml of hydrochloric acid (0.01 N) and immediately placed into the dialysis membrane. The bags were closed and placed into the basket of the dissolution apparatus.

Then, the basket was immersed in 100 ml of 0.01 N HCl and the dissolution test was carried out at a temperature of 37° C. with a rotation speed of 75 rpm/min, withdrawing, at appropriate times, samples of dissolution phase that were immediately replaced with fresh solvent in order to maintain constant sink condition. The withdrawn samples were spectrophotometrically analyzed after colorimetric reaction following the method reported in paragraph 2.

Figure 3:
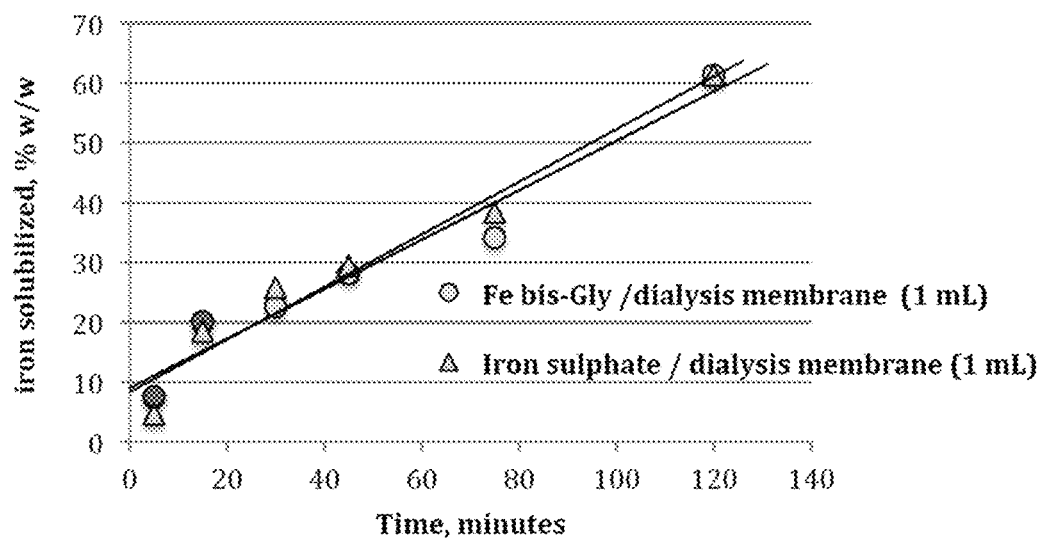
FIG. 3: Dissolution rate of iron salts/dialysis membrane (example 5)

The results of the dissolution test for the iron salts are reported in FIG. 3 and in Table 4, as an average percentage of solubilized iron vs time (n=3).

The results of the dissolution test showed a rapid solubilization of the bis-glycinate iron salt: in fact, after 15 minutes from the beginning of the experiment the amount of iron dissolved in the medium was about 20% of the total content. Then, the solubilization rate followed a linear trend with a dissolution rate of 0.378 $min^{-1}$ reaching a percentage of dissolved iron of about 60% after 120 minutes. A similar dissolution profile was determined for iron sulphate: the dissolution rate was 0.439 $min^{-1}$ and the percentage of iron in solution after 120 minutes was about 61%.

TABLE 4

Amount of solubilized iron from iron salts in acidic medium

| Time (minutes) | iron bisglycinate Solubilized iron (1.0 mL) (% w/w) Mean ± sd, n = 3 | iron sulphate Solubilized iron (1.0 mL) (% w/w) Mean ± sd, n = 3 |
|---|---|---|
| 5 | 7.528 ± 0.414 | 4.501 ± 0.707 |
| 15 | 20.124 ± 2.030 | 18.291 ± 1.432 |
| 30 | 22.580 ± 0.218 | 25.616 ± 1.850 |
| 45 | 28.165 ± 2.768 | 29.352 ± 1.747 |
| 75 | 34.095 ± 1.528 | 38.293 ± 6.689 |
| 120 | 57.900 ± 1.504 | 61.207 ± 6.672 |

4. Determination of the Dissolution Profile of the Complex Iron Bisglycinate with Alginc Acid Sodium Salt (Feralgina®)

Figure 4:
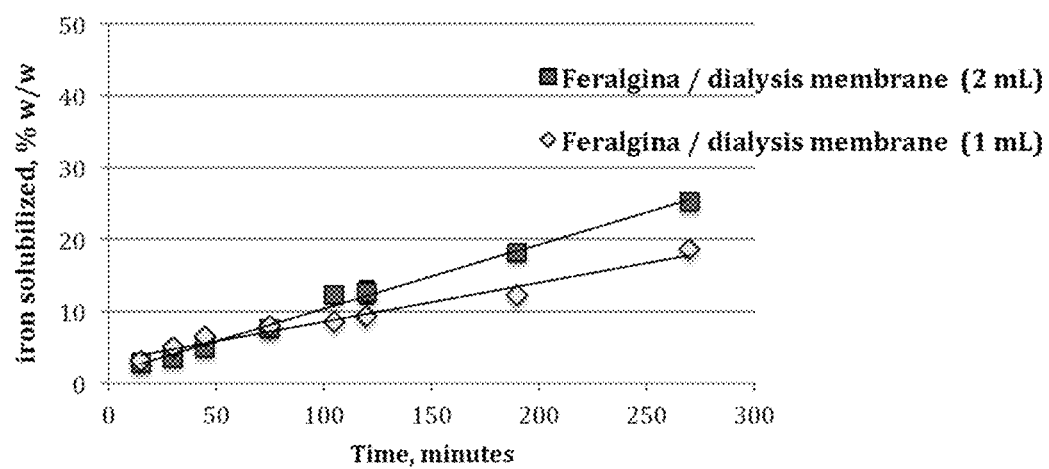
FIG. 4: Dissolution rate of iron from Feralgina®/dialysis membrane (example 5)

Experimental method: after hydration of the dialysis membrane for one night in deionized water, three exactly weighted samples of Feralgina® having different weights (range 20-30 mg) were dissolved with 1.0 ml (method A) or with 2.0 ml (method B) of hydrochloric acid (0.01 N) and the resulting solutions were placed into the hydrated dialysis membrane. The bags were perfectly closed and placed into the basket of the dissolution apparatus. The dissolution test was performed according to what already reported in paragraph 3. The basket was immersed in 100 ml of 0.01N HCl at a temperature of 37° C., with a rotation speed of 75 rpm/min, collecting samples of dissolution medium at appropriate times immediately replaced with fresh solvent in order to keep the dissolution constant (sink condition). The withdrawn samples were analyzed spectrophotometrically after colorimetric reaction following the method reported in paragraph 2. The results of the Feralgina® dissolution tests are shown in FIG. 4 and Table 5, as percentage of solubilized iron vs time (n=3).

The results of the iron dissolution test from the Feralgina® complex based on iron bis-glycinate and alginic acid sodium salt showed a certain degree of difference in the dissolution profiles of iron when the different experimental conditions were performed. The different dissolution rates were obtained: 0.0543 and 0.0898 $min^{-1}$ for the dissolution process of Feralgina® in 1.0 ml (method A) and in 2.0 ml (method B) of hydrochloric acid, respectively.

The presence of a greater volume of hydrochloric acid into the dialysis membrane seemed to facilitate the solubilization process of iron.

TABLE 5

Amount of solubilized iron from co-processed complex Feralgina ® in different amount of acidic medium

| Time (minutes) | Solubilized iron (1.0 mL) (% w/w) Mean ± sd, n = 3 | Solubilized iron (2.0 mL) (% w/w) Mean ± sd, n = 3 |
|---|---|---|
| 15 | 3.071 ± 0.708 | 2.843 ± 0.360 |
| 30 | 4.926 ± 0.833 | 3.455 ± 0.397 |
| 45 | 6.452 ± 0.914 | 4.876 ± 0.339 |
| 75 | 7.824 ± 0.107 | 7.584 ± 0.369 |
| 105 | 8.567 ± 0.424 | 12.224 ± 0.468 |
| 120 | 9.226 ± 0.188 | 12.548 ± 1.572 |
| 190 | 12.105 ± 0.617 | 18.143 ± 0.686 |
| 270 | 18.553 ± 0.947 | 25.239 ± 0.646 |

5. Determination of the Iron Dissolution Profile from Commercial Products (TecnoFERPlus e Ferrograd)

The dissolution tests of TecnoFERPlus were performed with two different experimental methods that involved, in one case, the use of the dialysis membrane and experimental conditions similarly to those followed for iron sulfate and iron bisglycinate with different volumes of hydrochloric acid 0.01N, and in the second one, the use of TecnoFERPlus (capsule) without the dialysis membrane.

Figure 5:
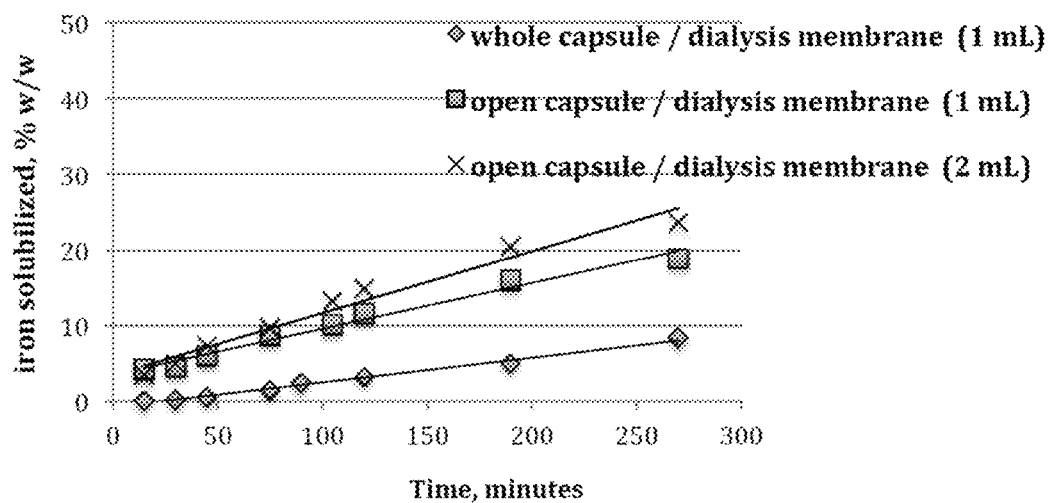
FIG. 5: Dissolution rate of iron from TecnoFERPlus/dialysis membrane (example 5)
Figure 6:
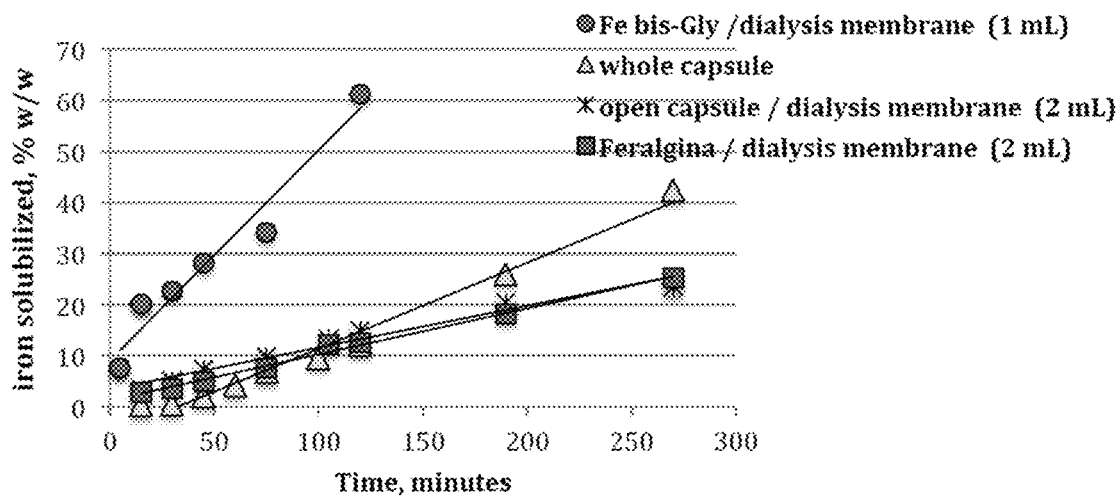
FIG. 6: Dissolution rate of iron from TecnoFERPlus (example 5)

Furthermore, TecnoFERPlus capsule (or its content) was intoduced into the dialysis membrane while FerroGrad tablet was directly introduced into the basket following the same dissolution procedure. The results of the dissolution tests are shown in FIGS. 5 and 6 and Table 6, as a percentage of solubilized iron as a function of time (n=3).

TABLE 6

Amount of solubilized iron from TecnoFERPlus in acidic medium using different experimental conditions

| Time (minutes) | whole capsule/ dialysis membrane (1.0 ml) (% w/w) Mean ± sd, n = 3 | open capsule/ dialysis membrane (2.0 ml) (% w/w) Mean ± sd, n = 3 | open capsule/ dialysis membrane (1.0 ml) (% w/w) Mean ± sd, n = 3 | whole capsule (1.0 ml) (% w/w) Mean ± sd, n = 3 |
|---|---|---|---|---|
| 15  | 4.162 ± 0.141  | 3.585 ± 0.194  | 0.050 ± 0.012 | 0.203 ± 0.089 |
| 30  | 4.449 ± 0.111  | 5.169 ± 0.144  | 0.206 ± 0.023 | 0.464 ± 0.138 |
| 45  | 5.972 ± 0.049  | 7.470 ± 0.060  | 0.539 ± 0.026 | 2.006 ± 0.761 |
| 75  | 8.639 ± 0.062  | 9.949 ± 0.073  | 1.415 ± 0.050 | 6.777 ± 0.423 |
| 105 | 10.091 ± 0.059 | 13.478 ± 0.083 | 2.361 ± 0.739 | 9.528 ± 1.154 |
| 120 | 11.571 ± 0.222 | 15.524 ± 0.302 | 3.209 ± 0.234 | 12.150 ± 1.666 |
| 190 | 15.971 ± 0.109 | 20.340 ± 0.150 | 5.001 ± 0.220 | 26.004 ± 5.486 |
| 270 | 18.793 ± 0.491 | 23.923 ± 0.646 | 8.301 ± 0.403 | 42.310 ± 4.881 |

The results showed that when the dissolution test is performed on the whole capsule in the presence of the dialysis membrane, the iron is slowly solubilized with a dissolution rate of 0.0325 min$^{-1}$ and with very low solubilized percentage of solubilized iron: after 120 minutes only 3% of iron content was detected in the dissolution medium and after 120 minutes the amount of dissolved iron was less than 10% (FIG. 5). A careful visual analysis of the behaviour of the capsule placed in the dialysis membrane in hydrochloric acid highlighted the formation of a partially gelled mass from which iron probably dissolved with more difficulty.

When the entire content of the capsule were placed in hydrochloric acid inside the dialysis membrane (open capsule), a more rapid dissolution rate of the iron was observed; in fact after 120 minutes from the beginning of dissolution test, a percentage of iron in solution between 10 and 15% of the total content was detected and this percentage probably depended, even if not significantly, on the amount of hydrochloric acid in contact with the solid (volume 1.0 or 2.0 ml). In fact, the dissolution rates calculated for linear interpolation of the experimental points were 0.0606 and 0.0818 min$^{-1}$ for the test performed on the open capsules in presence of 1.0 and 2.0 ml of hydrochloric acid inside the dialysis membrane, respectively.

Furthermore, after 270 minutes, the amount of iron dissolved in an acid dissolution medium was comparable (about 20%) with that obtained by dissolving Feralgina® (0.0898 min$^{-1}$) (see FIG. 6).

The dissolution profiles, shown in FIG. 6, evidenced that the dissolution of the iron from the whole capsule of commercial TecnoFERPlus performed in HCl 0.01N, is constant and linear as a function of time, reaching over 40% of the total iron dissolved after 270 minutes. The presence of the gelatine capsule, pharmaceutical form, had a limited influence on the solubilization of iron, exclusively affecting the first 30 minutes of testing, when the amount of solubilized iron was 10% lower than that solubilized for open capsule in the presence of the membrane to dialysis (2.0 ml). The influence of the gelatine capsule was negligible since the good linearity of the dissolution profile (R2=0.983) and the higher percentage of dissolved iron at the end of the test were obtained.

6. Conclusions

The higher iron bioavailability achieved with iron bisglycinate chelate sodium alginate than with bis-glycinate iron, as shown in example 4, is plausibly due to the fact that the former has a slower dissolution that could determine a more prolonged absorption of iron at the intestinal level over time.

This can be explained by the fact that the DMT1 receptor, reputed to the absorption of iron in the duodenum, is a saturable receptor whose ability to absorb iron is linked to the receptor saturation: therefore, the presence of a large amount of iron available to the DMT1 receptors per unit of time (as for instance provided by administering an iron bis-glycinate chelate) immediately saturates the receptors themselves, with the consequence that a portion of the iron dissolved in the gastric juice is not absorbed, due to the saturation of the receptors, and it is thus eliminated through the gastrointestinal tract.

To the contrary, by orally administering iron bis-glycinate chelate sodium alginate, iron is released more gradually; it reaches therefore the duodenum in a slower and steady way, ultimately allowing DMT-1 receptors to function in a continuous way, because they are never fully saturated and consequently increasing the iron bioavailability.

The invention claimed is:

1. A method for treating sideropenic anaemia in humans, comprising administering ferrous bis-glycinate chelate sodium alginate at a daily dose corresponding to 30 mg of iron to a subject in need thereof, wherein the weight ratio between the ferrous bis-glycinate chelate and sodium alginate is 1:1.

2. A method for increasing the absorption of iron in humans, comprising administering ferrous bis-glycinate chelate sodium alginate at a daily dose corresponding to 30 mg of iron to a subject in need thereof, wherein the weight ratio between the ferrous bis-glycinate chelate and sodium alginate is 1:1.

3. A method for treating sideropenic anaemia in humans, comprising administering to a subject in need thereof a product obtained by spray-drying an aqueous solution comprising ferrous bis-glycinate chelate sodium alginate, wherein the weight ratio between the ferrous bis-glycinate chelate and sodium alginate is 1:1, and the daily dosage of ferrous bis-glycinate chelate and sodium alginate corresponds to 30 mg of iron.

4. The method according to claim 3, wherein the sodium alginate has a molecular weight between 10,000 and 350,000 Da.

5. The method according to claim 3, wherein said product has a particle size of less than 20μ.

6. The method according to claim 3, wherein said product has a density between 0.2 g/ml and 0.8 g/ml.

7. The method according to claim 3, wherein said product further comprises an antioxidant.

8. The method according to claim 7, wherein said antioxidant is ascorbic acid.

9. The method according to claim 7, wherein said antioxidant is in an amount lower than 0.5% with respect to the total weight of the ferrous bis-glycinate chelate sodium alginate.

10. The method according to claim 1, wherein the sodium alginate has a molecular weight between 10,000 and 350,000 Da.

11. The method according to claim 2, wherein the sodium alginate has a molecular weight between 10,000 and 350,000 Da.

* * * * *